(12) United States Patent
Paul

(10) Patent No.: US 9,918,759 B2
(45) Date of Patent: Mar. 20, 2018

(54) BONE TREATMENT IMPLANTS, AND SPRINGS THEREFORE

(71) Applicant: Kamaljit S. Paul, Oshkosh, WI (US)

(72) Inventor: Kamaljit S. Paul, Oshkosh, WI (US)

(73) Assignee: Kamaljit S. Paul, Oshkosh, WI (US)

( * ) Notice: Subject to any disclaimer, the term of this patent is extended or adjusted under 35 U.S.C. 154(b) by 580 days.

(21) Appl. No.: 14/540,822

(22) Filed: Nov. 13, 2014

(65) Prior Publication Data

US 2015/0134013 A1 May 14, 2015

Related U.S. Application Data

(60) Provisional application No. 61/903,700, filed on Nov. 13, 2013.

(51) Int. Cl.
*A61B 17/80* (2006.01)
*A61F 2/44* (2006.01)
*A61F 2/30* (2006.01)

(52) U.S. Cl.
CPC ........ *A61B 17/8042* (2013.01); *A61F 2/4455* (2013.01); *A61F 2002/30505* (2013.01); *A61F 2002/30787* (2013.01); *A61F 2002/4475* (2013.01)

(58) Field of Classification Search
CPC .................... A61B 17/7291; A61B 17/8042
See application file for complete search history.

(56) References Cited

U.S. PATENT DOCUMENTS

| 6,755,833 | B1 | 6/2004 | Paul | |
|---|---|---|---|---|
| 7,008,426 | B2 | 3/2006 | Paul | |
| 7,070,599 | B2 | 7/2006 | Paul | |
| 7,204,837 | B2 | 4/2007 | Paul | |
| 7,255,699 | B2 | 8/2007 | Paul | |
| 8,221,476 | B2 | 7/2012 | Paul | |
| 8,454,666 | B2 * | 6/2013 | Tornier | A61B 17/8042 606/289 |
| 9,039,744 | B2 * | 5/2015 | Goodman | A61B 17/7059 606/246 |
| 2005/0021032 | A1 * | 1/2005 | Koo | A61B 17/7059 606/295 |

(Continued)

FOREIGN PATENT DOCUMENTS

FR 2794963 12/2000

*Primary Examiner* — Andrew Yang
(74) *Attorney, Agent, or Firm* — Thomas D. Wilhelm; Northwind IP Law, S.C.

(57) ABSTRACT

Springs for use in bone implant assemblies where the spring is assembled to a bone implant body. The spring comprises first and second bands, biased against each other, by a spring leaf which extends between the bands, and resists compression of the bands toward each other. Securement of the spring to the implant body can provide for initial transverse movement of the entire length of the spring leaf, when one of the bands is urged toward the other. When assembled to an implant body, the bands extend into fastener receiving apertures in the implant body. A stud is installed in the implant body and extends into an aperture in the spring. A stud-receiving aperture in the spring is optionally elongate, with the length of such aperture extending along the width of the spring, thereby enabling distributing an external compressive force through substantially the entire body of the spring leaf.

53 Claims, 14 Drawing Sheets

(56) References Cited

U.S. PATENT DOCUMENTS

| | | |
|---|---|---|
| 2006/0161157 A1 | 7/2006 | Mosca et al. |
| 2006/0229620 A1 | 10/2006 | Rothman et al. |
| 2007/0123884 A1 | 5/2007 | Abdou |
| 2009/0088808 A1 | 4/2009 | Lindemann et al. |

* cited by examiner

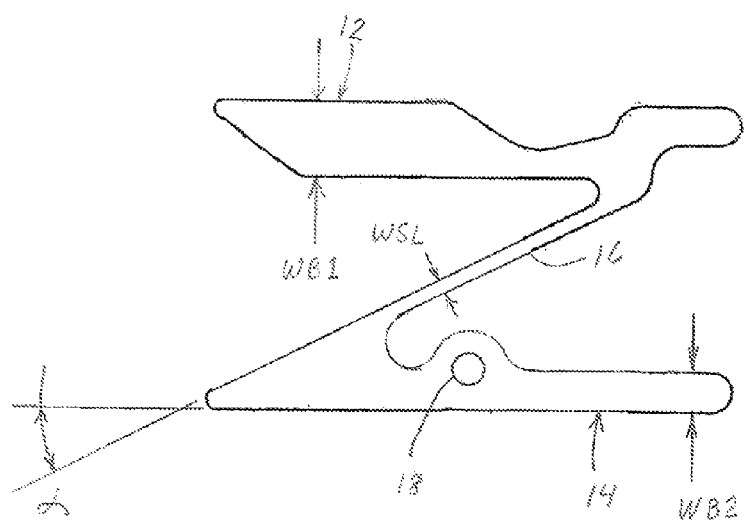

BONE TREATMENT IMPLANTS, AND SPRINGS THEREFORE

REFERENCE TO RELATED APPLICATION

This application is a Non-Provisional of U.S. Provisional Patent Application No. 61/903,700, filed Nov. 13, 2013, the complete disclosure of which is incorporated herein by reference, in its entirety.

BACKGROUND

The present invention relates to devices for the fixation and/or support and/or replacement of bone structure. In particular, the present invention relates to bone treatment implant assemblies, including a bone treatment implant body and one or more spring structures, all directed to treatment, stabilization and/or replacement of bones of e.g. the spinal column or stabilization of long bones.

Specifically, this invention is directed toward failure avoidance, namely toward avoiding bone screws in surgical implant assemblies from backing out of, withdrawing from the implant assembly and/or bones to which they have been mounted, thus preventing e.g. nerve, muscle, and/or vascular damage which can be done by such withdrawn screw.

Implant assemblies of the present invention have particular application in situations where compression or settling forces, as well as torsional and flexing forces, of e.g. "fixed" vertebrae or a long bone, on a bone treatment implant assembly, cause significant stressing and potential failure of one or more elements of the bone treatment implant assembly, or unacceptable stressing or other deleterious effect on the bones being treated.

Bone fixation and bone replacement have become common approaches for treating bone-related disorders, fractures, and the like, and for fusion of vertebrae at the time such fixation is instituted. Namely, one or more bones or bone fragments may be fixed in position relative to one or more other bones or bone fragments. Generally, a bone treatment implant, e.g. a spinal plate, is the device of choice used for mechanically supporting cervical vertebral fixation. Lower in the spine, implants known as "cages" may be used to replace deteriorated natural bone structure.

A typical implant plate includes an implant body having a plurality of apertures therethrough. A plurality of fasteners, e.g. bone screws, are generally positioned into and through respective ones of the apertures of the implant to thereby attach the implant to bone, such as to two or more respective upper and lower supporting adjacent spinal vertebrae. The screws are fastened to the respective support vertebrae to thereby attach the implant body to healthy supporting bone structure in the patient. In general, such implant assemblies can be utilized, for example, for fixation of cervical, lumbar, and/or thoracic portions of the spine.

The basis of implant fixation is to use screws to solidly mount the implant body to healthy bone tissue, thus to provide support to the bone structure being treated. In addition to the application of, for example and without limitation, a spinal plate or cage, bone graft material may be combined with the vertebrae, or vertebrae elements, as an assist in permanently fusing together adjacent vertebrae or other bone material. The graft material can consist of bone graft material obtained from bones of the recipient, or bone graft material obtained from another individual.

A common problem associated with the use of such bone implants is the tendency of the bone screws to "back out" or pull away or otherwise withdraw from the natural bone or bones into which the screws are mounted. This problem of "backing out" occurs primarily as a response to the normal motions of the body skeleton as the patient goes about his or her daily activities/routine. This is a particularly important problem in that, as screws become loose and pull away or withdraw from the bone, the heads of the screws can rise above the surface of the implant and, possibly, even work their way completely out of the bone. While this condition can cause extreme discomfort for the recipient user of the implant assembly, namely the patient, any substantial withdrawal of the screws from the bone/implant can also create a number of potentially serious physiological problems if and when withdrawn portions of such screws interact with the significant amount of nervous and vascular tissues located at or near the implant site in the body.

A number of plate assembly designs and cage assembly designs have been proposed in attempts to prevent screws from pulling away from, or withdrawing from, the bone and/or to prevent the screws from backing out of, or pulling away from, or withdrawing from, the surface of the implant assembly. Such mechanisms used to stabilize the position of the implant and/or the bone screws include a cam which engages the screw, alternately a cap mounted to overlie the bone screw, alternately a bone screw having a head which bites into the side wall of the implant body aperture, alternately a cover screw whose head overlies an adjacent bone screw, alternately knives which are rotated so as to cut into healthy bone tissue after placement and securement of the implant assembly, and alternately springs which intrude into the withdrawal path of the bone screws.

All of these designs have certain limitations, including parts releasing from the implant assembly, potential for breakage of a screw, or assemblies which require particular precision and alignment in their application or implementation in order to work as intended. Additionally, loose components and accessories of spinal implant assemblies, which address the "backing-out" or withdrawal problem, can get dropped and/or misplaced during the fixation surgical procedure, prolonging and complicating the procedure which results in increased risk of harm to the patient.

Yet another common phenomenon associated with the use of such spinal implant assemblies is the tendency, of vertebrae which are being treated, to settle after the implant assembly has been installed. Such settling may add compression forces to the above-listed forces. In some embodiments of bone implants, slots may be used in the implant body to accommodate such settling, thus to limit the amount of stress imposed on the screws.

It would be desirable to provide bone treatment implant assemblies which facilitate secure bone-to-implant fixation and/or support, such as at e.g. adjacent or second adjacent vertebrae, while providing screw back-out protection structure which is securely fixed to the implant body and which enhances stabilization of the implant assembly in the living body.

It would further be desirable to provide bone treatment implant assemblies which afford substantial protection against pulling away or withdrawal of mounting screws, which pulling away or withdrawal may result from e.g. torsional movement, flexing movement, or stress and/or dynamic load sharing of the bone being treated, the protection thereby enhancing the bone rebuilding process carried on routinely by the living body.

It would be still further desirable to provide bone treatment implant assemblies comprising an implant body and a back-out prevention structure having resiliently movable spring-like members, having resilient properties, the assemblies being so mounted and positioned as to enable bone screws to move past such spring-like members, with corresponding flexing or other movement of such spring-like members, when the bone screws are being installed in a patient and which, in combination with the designs of the bone screws, prevent unintentional withdrawal of the bone screws after installation of the bone screws in the patient being treated.

It would be still further desirable to provide a spring structure, both alone and in a bone treatment implant assembly comprising a bone treatment implant body, wherein the spring structure includes resiliently movable spring-like material having resilient properties, including a spring leaf, wherein the spring structure is secured, at least in part, to the implant at the spring leaf.

It would be yet further desirable to provide a spring structure wherein the spring structure is secured, at least in part to the implant body at the spring leaf, in combination with enabling limited movement of the spring leaf relative to the implant body, and further enabling passing such limited movement from the spring leaf to the spring bands.

It would be yet further desirable to enable such limited spring movement by use of an aperture in the spring leaf, spaced from opposing ends of the leaf, and wherein a stud extends from the implant body into, optionally through, the aperture.

It would optionally be desirable to provide such limited spring movement by use of a spring leaf structure having an intermediate anchor element which is located beyond the longitudinal ends of the bands such that the bands can be fully enclosed within a channel in the implant body while the anchor element is fixedly secured to the implant body at the end of the channel.

It would be further desirable to provide bone treatment implant assemblies, such as spinal plate assemblies or spinal cages, which can be completely pre-assembled such that no assembly steps need be performed on the implant assembly, itself, as part of the surgical procedure wherein the implant assembly is being installed in a patient.

It would be still further desirable to provide bone treatment implant assemblies wherein apparatus, in such bone treatment implant assemblies, for preventing withdrawal of bone screws from the bone, after installation of the bone screws in a patient, are automatically activated, to prevent such withdrawal, as a consequence of the installation of suitably-configured such bone screws.

SUMMARY

This invention provides novel bone implant assemblies and springs suitable for use in such assemblies, methods of assembling such bone implant assemblies, and methods of using such bone implant assemblies. Such bone implant assembly comprises a spring structure assembled to a bone treatment implant body. The spring structure comprises first and second elongate bands, biased against each other, by a spring leaf which extends between the bands, and resists compression of the bands toward each other. When the bands are moved toward each other, the spring leaf resiliently urges the bands away from each other. In the process of assembling a spring to an implant body, the bands are juxtaposed proximate, and extend into, fastener-receiving-apertures in the implant body. Width of the spring leaf is less than height of the spring leaf, whereby the ratio of spring leaf width to spring leaf height is less than 1/1. Protuberances may extend from one or both bands, and engage detents in the plate, thereby to arrest and/or prevent longitudinal movement of the spring structure relative to the plate. In the alternative, a stud may be installed in the implant body and extend into and/or through an aperture in the spring leaf, or an aperture in one of the bands. Such stud can be retained in the implant body by a friction fit, optionally using a spot-weld to further secure the stud to the implant body. The stud-receiving aperture in the spring is optionally elongate, with the longitudinal axis of the aperture extending along the width of the spring, thereby to enable distributing an external compressive force through substantially the entire length of the spring leaf.

The invention comprehends a spring structure far use with a bone repair implant, the spring structure having first and second ends, a length and a width, a spring structure top and a spring structure bottom, the spring structure comprising first and second bands, each having a band top associated with the spring structure top, and a band bottom associated with the spring structure bottom, the bands having respective first and second ends, said first and second bands having first and second outer edges facing outwardly of the spring structure and collectively defining the width of the spring structure; a spring leaf extending between the first and second bands, the spring leaf having a spring top and a spring bottom; and an aperture extending through the spring structure, from the top of the spring structure to the bottom of the spring structure.

In some embodiments, the aperture extends through the spring leaf.

In some embodiments, the spring leaf extends in a generally constant direction the first band to the second band.

In some embodiments, the spring leaf extends in a first direction from the first band to the aperture, and in a second substantially different direction from the aperture to the second band.

In some embodiments, the aperture has a length and a width, the length of the aperture being greater than the width of the aperture, and the length of the aperture extends along the width of the spring structure.

In some embodiments, the spring leaf has a spring leaf width, and there is a substantial enlargement of the spring leaf width at the aperture.

In some embodiments, the aperture extends through the second band.

In some embodiments, the second band has a band width, and there is a substantial enlargement of the band width at the aperture.

In some embodiments, the outer edge of said first band having a first outermost edge portion which, in part, defines the width of said spring structure, and a first recessed portion, said first recessed portion being located intermediate the length of said spring structure and spaced from both of the first and second ends of said spring structure.

In some embodiments, the first recessed portion is internally symmetric such that a profile of a longitudinally extending first half of the first recessed portion can be overlaid over a profile of a longitudinally extending second half of the first recessed portion, and the profile of the overlying first half substantially matches the profile of the underlying second half.

In some embodiments, the first recessed portion of the first band comprises a first shoulder element extending from a first end thereof at the outermost edge of the first band to a second end thereof directed in a first direction, a first intermediate neck element having a third end extending from the second end of the shoulder element in a second different direction away from the first outermost edge to a fourth end, and a first relief element having a fifth end extending from the first neck element in a third direction toward the outermost edge of the first band.

In some embodiments, the outer edge of the second band has a second outermost edge portion which, in part, defines the width of the spring structure, the outer edge of the second band further has a second recessed portion, the second recessed portion of the second band comprising a second shoulder element extending from a sixth end at the outermost edge of the second band to a seventh end directed in a fourth direction, a second intermediate neck element having a eighth end extending from the seventh end of the second shoulder element in a fifth different direction away from the second outermost edge to a ninth end, and a second relief element having an tenth end extending from the second neck element in a sixth direction toward the outermost edge of the second band.

In some embodiments, the first and second shoulder elements are disposed toward the first end of the spring structure.

In some embodiments, the first and second shoulder elements are disposed toward opposing ones of the first and second ends of the spring structure.

In some embodiments, the invention comprehends a bone repair implant assembly comprising an implant body having a length, and an implant wall defining a top of the implant body, a channel extending along the length of the implant body in the implant wall, the channel having a bottom wall and opposing side walls, a stud aperture extending into the implant wall from the bottom wall of the channel, a spring structure of the invention being disposed in the channel with the aperture in the spring structure overlying the stud aperture, a stud being fixedly positioned in the stud aperture and extending into the aperture in the spring structure.

In some embodiments, the implant assembly further comprises a bone screw extending through a bone screw receiving aperture in the implant body and interacting with the spring structure, further comprising a second spring structure of the invention disposed in the channel, with the aperture in the second spring structure overlying a second stud aperture which extends into the implant wall of said implant body from the bottom wall of the channel, a second stud being fixedly positioned in the second stud aperture and extending into the aperture in the second spring structure, a second bone screw extending through a second bone screw receiving aperture in the implant body and interacting with the second spring structure.

In some embodiments, the implant assembly further comprises a bone screw extending through a bone screw receiving aperture in said implant body and interacting with the spring structure, further comprising a second channel extending along the length of the implant body in the implant wall, the second channel having a second bottom wall and second opposing side walls, a second stud aperture extending into the implant wall from the bottom wall of said second channel, a second spring structure of the invention being disposed in the second channel with the aperture in the second spring structure overlying the second stud aperture, a second stud being fixedly positioned in the second stud aperture and extending into the aperture in the second spring structure, a second bone screw extending through a second bone screw receiving aperture in the implant body and interacting with the second spring structure.

BRIEF DESCRIPTION OF THE DRAWINGS

FIG. 4D shows a top view of a sixth embodiment of springs of the invention.

Figure 1:
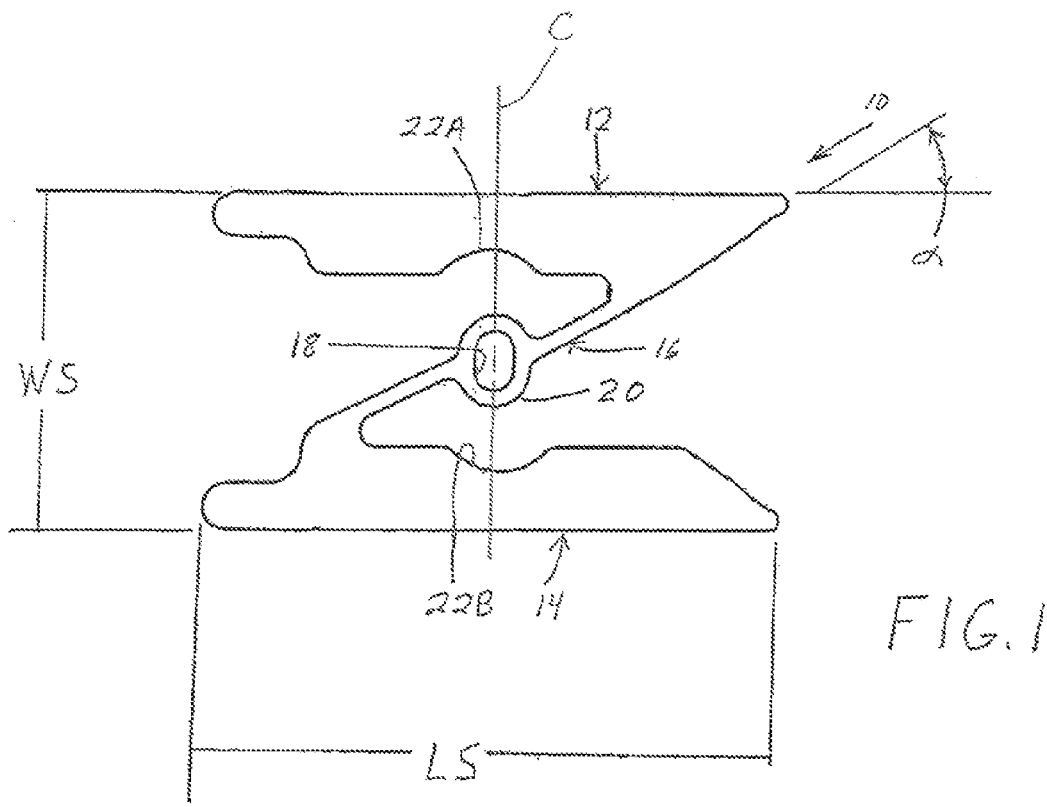
FIG. 1 shows a top view of a first embodiment of springs of the invention.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Figure 1A:
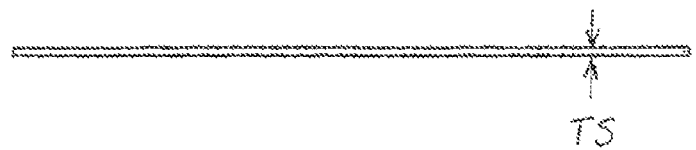
FIG. 1A shows an edge view of the spring illustrated in FIG. 1.

Referring now to the drawings, FIGS. 1 and 1A show a top view and an edge view, respectively, of a spring 10 of the invention which can be used in a variety of surgical implants to prevent bone screws from backing out of the bone tissue to which the surgical implant is surgically mounted. Spring 10 has a length "LS" and a width "WS", and a thickness "TS" perpendicular to both the length and the width.

First and second opposing elongate bands 12, 14 extend parallel to each other in a common plane or in a common curved surface, and define opposing outside edges of spring 10.

An imaginary centerline "C" extends across the width of the spring structure, thereby defining a first half of the spring structure corresponding to a first end of the spring structure, and an opposing second half of the spring structure corresponding to an opposing second end of the spring structure.

In the embodiment shown in FIGS. 1 and 1A, a generally straight single spring leaf 16 is connected to, and extends from, first band 12 in the first half of the spring structure, extending to second band 14 in the second half of the spring structure. Imaginary extensions of the spring leaf intersect the outermost edges of bands 12 and 14 at angles α of about 20 degrees to about 35 degrees, e.g. about 30 degrees to the outermost edges of the respective bands. Spring leaf 16 operates as a compression spring such that, when a compression force urges bands 12, 14, from a rest condition, namely an unstressed condition, toward each other, the corresponding distortion of spring leaf 16 results in spring leaf 16 resisting such compression force. Spring 10, including bands 12 and 14, and spring leaf 16, represents a single piece part, and is typically, but riot necessarily, fabricated from a single work piece.

An aperture 18 extends through an enlargement 20 at the mid-section of spring leaf 16. Spring structure material entirely surrounds aperture 18 such that lateral entry into the aperture, e.g. from the side of the aperture, is precluded by the surrounding spring structure material. In the embodiment illustrated in FIG. 1, aperture 18 is longer in the width direction "WS" of the spring than in the length direction "LS" of the spring. Thus, aperture 18 is generally elongate, optionally having a generally constant width, except at the rounded ends of the aperture. Inner edges 22A, 22B of bands 12, 14 are recessed adjacent enlargement 20.

Figure 2:
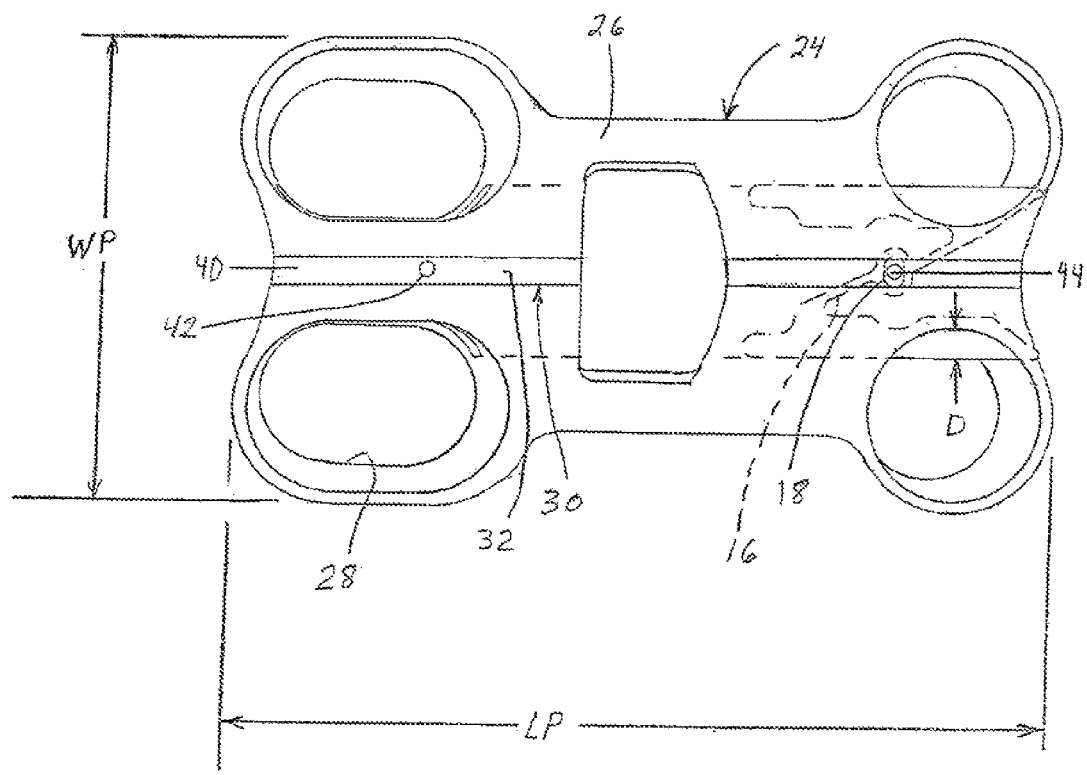
FIG. 2 shows a top view of a surgical plate assembly having a spring of FIG. 1 assembled thereto.
Figure 3:
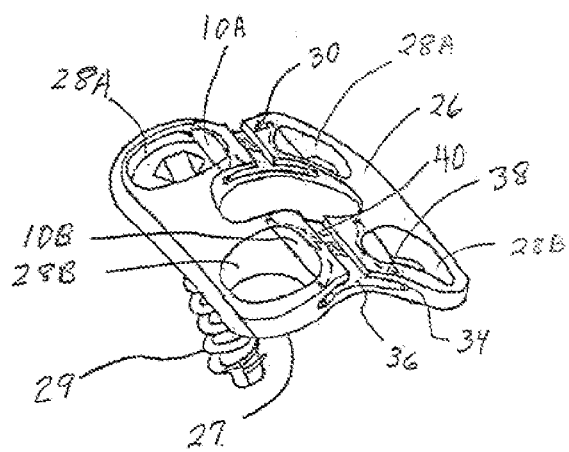
FIG. 3 shows a pictorial end view of a surgical plate assembly using a plate similar to the plate shown in FIG. 2.

FIGS. 2 and 3 show spring 10 of FIG. 1 mounted in first and second spinal plates 24, for example cervical plates which, in use in a patient, support cooperating bone structure in the cervical portion of the patient's spine.

Spinal plates 24 shown in FIGS. 2 and 3 have lengths "LP" and widths "WP", a top surface 26, and a bottom surface 27 which is adapted to be positioned adjacent bone structure of the patient in whom the respective spinal plate is surgically implanted. A plurality of bone-fastener-receiving apertures 28 receive bone screws 29. Apertures 28 are arranged in first and second rows of such apertures, the rows being aligned with the lengths of the spinal plates.

Figure 11:
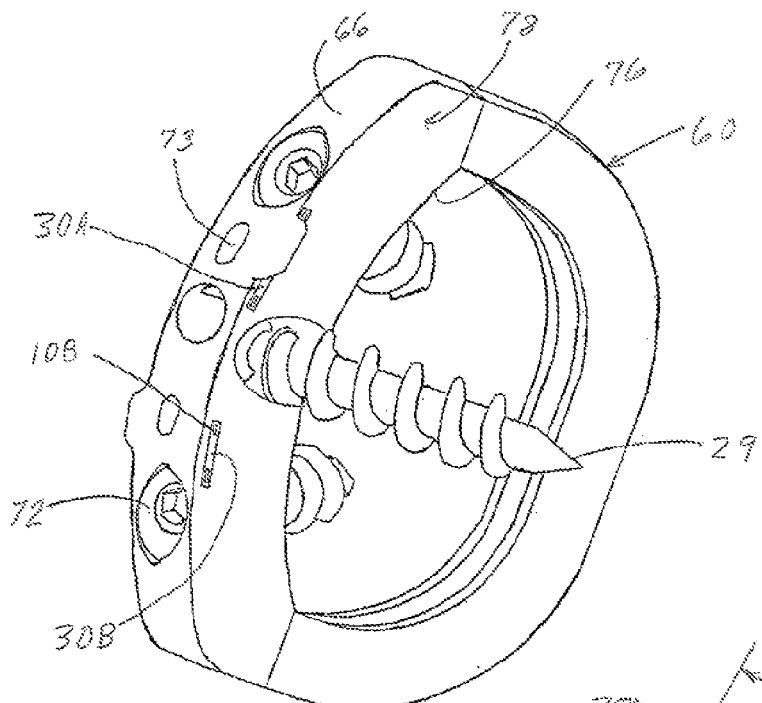
FIG. 11 shows a top pictorial view of a third spinal cage assembly, including three bone screws, a first spring as shown in FIG. 4C, and a second spring as shown in FIG. 4D.
Figure 12:
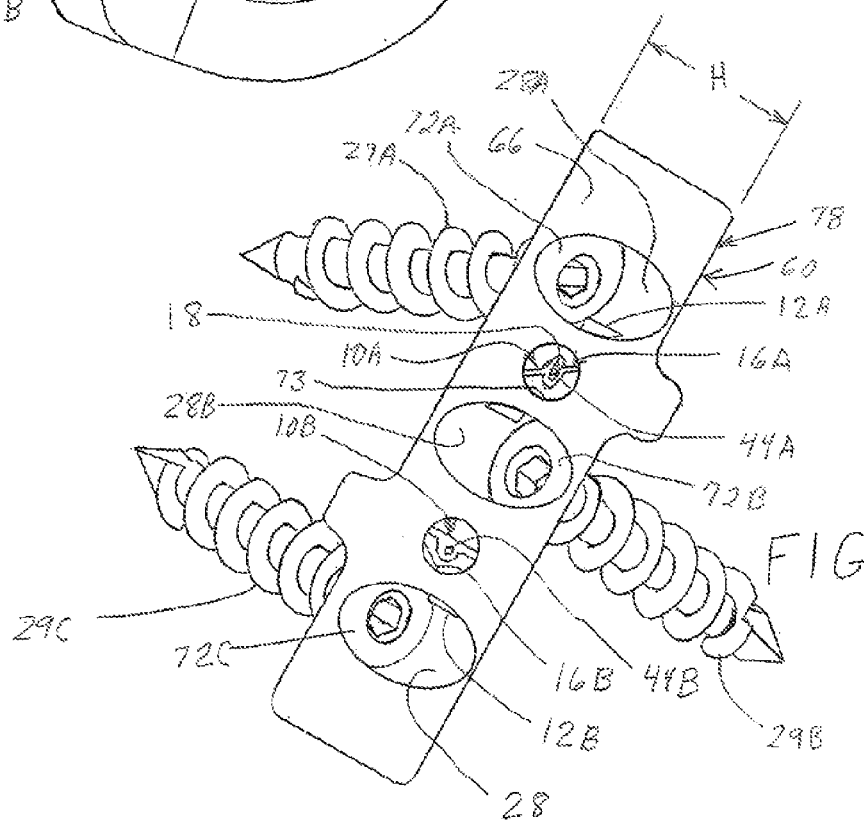
FIG. 12 shows a top view of the spinal cage assembly of FIG. 11.

Channels 30 extend along the lengths of the plates. Central portions of such elongate channels extend upwardly to, open up to, the top surfaces 26 of the plates. A such channel 30 has a bottom wall 32, opposing side walls 34, and has openings 36 at the respective ends of the spinal plate, as illustrated in FIG. 3. Channel 30 further has overhanging top walls 38 extending inwardly from the side walls of the channel and spaced from each other and from the bottom wall, thereby leaving the open slot 40 in the top of the channel between the overhanging top walls, and extending along the length of the channel. Open slot 40 can be expanded in width to be as wide as, or wider than, the locations of side walls 34 of the channel, or can be eliminated if desired wherein the top of the channel is completely closed by top walls 38, as illustrated in FIGS. 11 and 12, or a channel can be partially or mostly closed at the top of the plate as in FIG. 2A, so long as adequate structure is employed, whether as part of the channel or as a feature of the spring, to hold spring 10 in a suitably fixed and useful position in channel 30. The three-dimensional space of the open cross-section of the channel, as defined between side walls 34 and top and bottom walls 38 and 32, is preferably generally constant along most, or substantially all, of that portion of the length of plate 24 which is occupied by channel 30 and where the channel is to be occupied by a spring 10. Side walls 34 of the channel are specifically located and configured such that the channel opens into the sides of apertures 28, and imaginary extensions of channel 30 extend inwardly into the aperture from the sides of, and across, the aperture. In general, and as illustrated in FIG. 2, imaginary extensions of side walls 34 project across apertures 28 at locations displaced inwardly of the aperture side walls by distances "D" of about 1 mm. Such inward displacement from the aperture side walls can be more or less than 1 mm, depending on structural dimensions of the cooperating elements of the assembly, such as the respective aperture and the respective bone screw.

A given spring, including bands 12, 14 and spring leaf 16 is typically fabricated from a single unitary generally planar work piece, of generally uniform thickness "TS". In such instance, the thickness of the work piece is also the thickness "TS" of the respective springs 10 which are fabricated from such work piece. The thickness of the spring leaf can be greater than, or less than, the thicknesses of the bands, but such is not normally the case.

Preferred method of fabricating the spring is to use laser cutting apparatus to cut away waste material so as to leave bands 12, 14, and spring leaf 16, including leaving the material at enlargement 20, namely around aperture 18.

Since the side walls of plate channel 30 open into screw apertures 28, bands 12, 14 extend across the respective apertures 28, as shown in FIG. 2, as the spring is being inserted into channel 30. The length of spring 10 as illustrated in e.g. FIG. 2 is at least long enough that bands 12, 14 extend across the apertures 28 far enough that the bands are impacted by a bone screw being driven through the respective screw aperture 28. In the embodiments illustrated in FIGS. 2 and 3, a separate spring is used for each of the side-by-side pairs of screw apertures 28. Thus, referring to FIG. 3, a first spring 10A is used adjacent the circular pair of apertures 28A at the distal end of the plate and a second spring 10B is used adjacent the slot-shaped pair of apertures 28B at the proximal end of the plate.

A stud aperture 42 extends through the plate, adjacent each pair of screw apertures 28 at any given location along the length of the plate. Stud aperture 42 is typically, but not necessarily, round. Stud aperture 42 extends, as a through-opening, from the bottom surface of the plate to bottom wall 32 of the channel 30. Stud aperture 42 is sized somewhat smaller than spring leaf aperture 18 such that the spring has limited capacity to move relative to the stud.

In assembling a given spring to the plate, an end of the spring is squeezed together e.g. to reduce width "WS" such that the width at the end of the spring is no greater than the width of the channel at the end of the plate where the spring is to be inserted into channel 30. With the width "WS" so reduced, the spring is inserted longitudinally into channel 30 and pushed along the length of the channel until the aperture 18 in the spring leaf lines up with the respective stud aperture 42.

With aperture 18 in the spring leaf aligned with stud aperture 42 in the implant, a stud 44 is inserted into the stud aperture such that the stud extends from a location at or proximate the bottom of the plate up through the thickness of the plate, and into the overlying stud aperture in the spring leaf, and thus into leaf aperture 16. The cross-section of stud 44 is typically, but not necessarily, configured so as to closely match the cross-section of aperture 42 in the plate, sufficiently closely to create at least moderate friction between the stud and the side walls of aperture 42, while fitting loosely into leaf aperture 18. With stud 44 extending through plate aperture 42, and into leaf aperture 18, the side wall of the stud faces those side wall surfaces of the spring leaf which define leaf aperture 18; and at least some portion of the stud surface is displaced from the side wall surfaces of aperture 18. Generally, but not necessarily, the top surface of the top end of the stud is aligned with, is in a common imaginary surface with, the top surface of the spring leaf.

Stud 44 can be held in aperture 42 entirely by friction between the sides of the stud and the side walls of aperture 42. However, a weld may be created, welding the bottom end of the stud to plate 24, typically at or proximate the bottom surface of the plate, whereby the weld enhances the fixation of the stud to the plate, in the stud aperture.

Figure 2A:
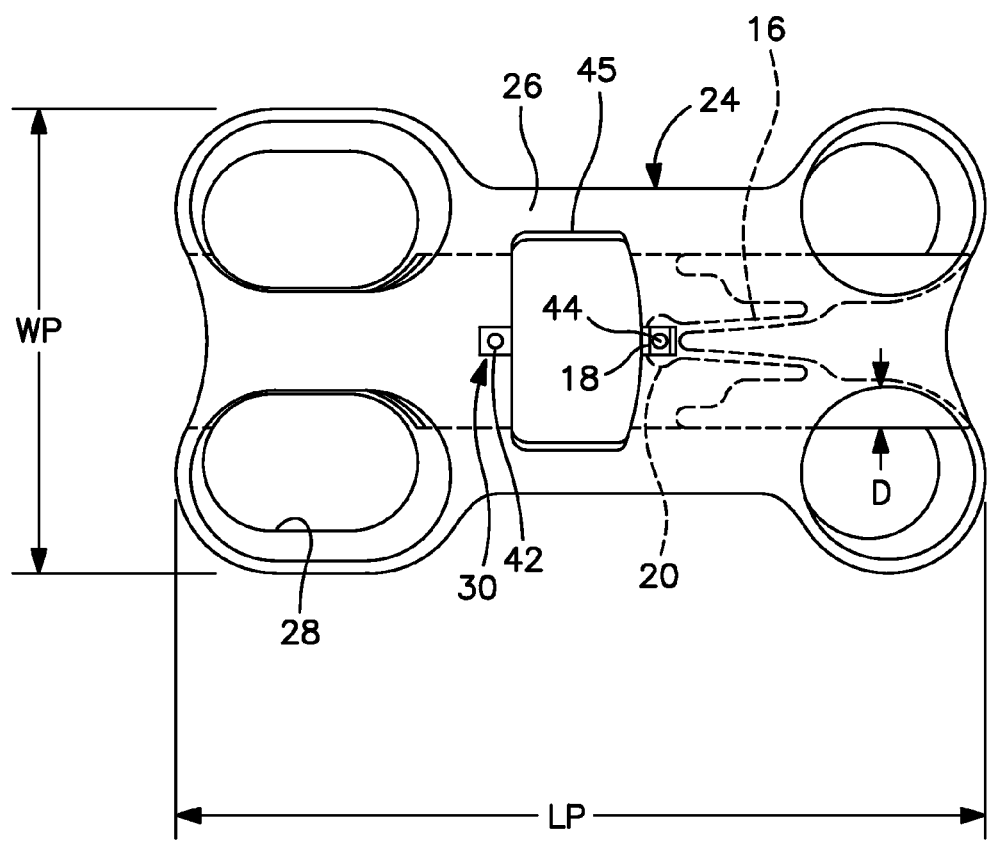
FIG. 2A shows a top view of a surgical plate assembly as in FIG. 2 but using a second embodiment of springs of the invention wherein the spring has an intermediate anchor element which is located beyond the longitudinal ends of the bands, the bands being enclosed within a dosed channel in the plate while an intermediate portion of the spring leaf is restrained at an open-topped end of the channel.

FIG. 2A shows a second embodiment of springs of the invention. The embodiment in FIG. 2A is similar to that of FIG. 2. However, channel 30 is largely enclosed, being open at its longitudinal ends and having a top opening only adjacent viewing aperture 45. Spring leaf 16 is "V-shaped", with leaf aperture 18 at an intermediate location along the length of the spring leaf, underlying the top opening in channel 30, overlying stud aperture 18 in the plate, and longitudinally beyond the ends of bands 12, 14. Aperture 18 is optionally elongate across the width of the spring as in the embodiment of FIGS. 1 and 2 so that the stress of an external compressive force, urging the bands together, can be distributed through the entire length of the spring leaf.

Figure 4A:
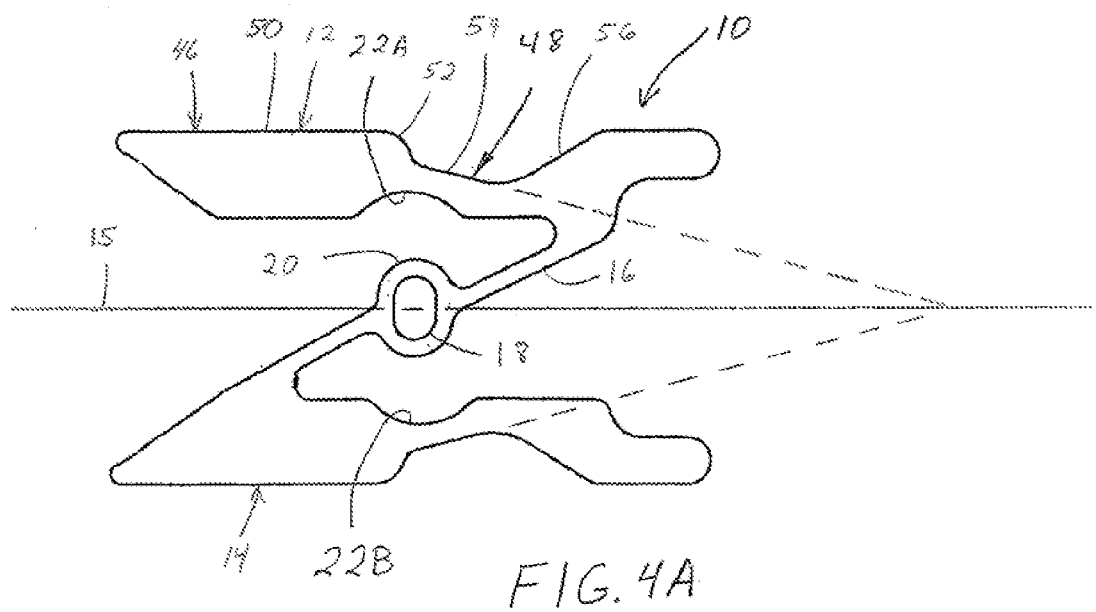
FIG. 4A shows a top view of a third embodiment of springs of the invention.

FIG. 4A illustrates a third embodiment of springs of the invention. In the FIG. 4A embodiment, a recessed portion 48 of the outer edge 46 of each band 12 or 14, intermediate the ends of the band, is recessed from the outermost portion 50 of the edge of the band. A given recessed portion includes an in-turned, and rounded, shoulder element 52, an inwardly-tapering neck element 54, and an outwardly-directed relief element 56. In the embodiment of FIG. 4A, the neck elements 54 of the recess portions on the opposing sides of the spring converge toward each other as shown by the dashed converging lines in FIG. 4A.

As in the embodiment of FIG. 1, first and second opposing elongate bands 12, 14 extend generally parallel to each other in a common plane or in a common curved surface, and define opposing outside edges of spring 10.

Also as in the embodiment of FIG. 1, a generally straight single spring leaf 16 is connected to, and extends between, bands 12 and 14, intersecting bands 12 and 14 at angles of about 20 degrees to about 35 degrees, e.g. about 30 degrees, to the outer edges of the respective bands.

Aperture 18 extends through enlargement 20 at the midsection of spring leaf 16. Aperture 18 is longer in the width direction of the spring than in the length direction of the spring. Thus, aperture 18 is generally mildly elongate, optionally having a generally constant width, except at the ends. However, in some embodiments, aperture 18 can be generally circular, thus having a similar dimension in each of the length and width directions of the spring.

Also as in the embodiment of FIG. 1, inner edges 22A, 22B of bands 12, 14 are recessed adjacent enlargement 20.

The spring illustrated in FIG. 4A differs from the spring illustrated in FIGS. 1-3 in that recessed portions 48 of the outer edges 46 of bands 12, 14, intermediate the ends of the bands, are recessed from the outermost portion 50 of the outer edge of the band. In the embodiment of FIG. 4A, the recessed portions are disposed toward, but displaced from, the right ends of bands 12, 14.

Recesses 48 are optional where the bone screw apertures are generally perpendicular to the top surface of the plate such as in FIGS. 2, 2A, and 3, such that the angles of the longitudinal axes of the bone screws are generally perpendicular to the top surface of the e.g. spinal plate 24. However, where the bone screws are to be driven into bone structure above and/or below the implant as in a lumbar cage implant assembly, bone screw apertures 28 extend at up and/or down angles relative to the implant where bone screws 29 enter apertures 28, whereby the top of such bone screw moves progressively, rather than substantially all at once, through the plane defined at the respective entrance surface of the respective aperture 28 where the screw enters the respective implant. In such use, the neck element and the relief element of the outer edge of the band 12 or 14 provide clearance and/or guidance for driving the bone screw shaft past the band and into aperture 28 at the desired angle; while shoulder element 52 provides initial and temporary interference relative to passage of the head of the bone screw as the bone screw is being driven into the overlying or underlying natural bone.

Figure 4B:
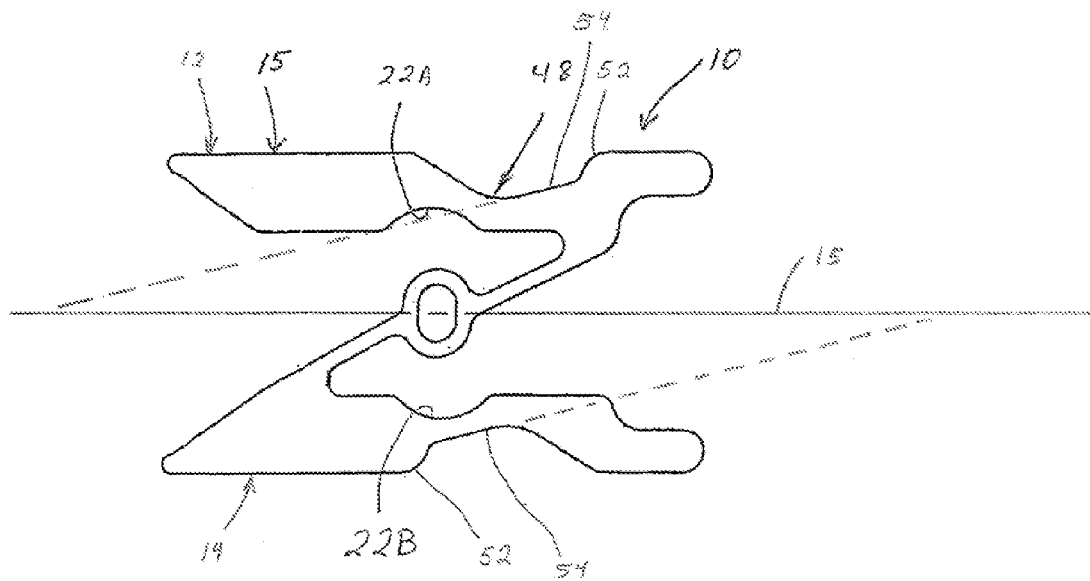
FIG. 4B shows a top view of a fourth embodiment of springs of the invention.

FIG. 4B shows a spring similar to the spring of FIG. 4A, except that the recessed portions 48 on bands 12, 14 are inverse images of each other. Namely, the recessed portion 48 of band 12 is an inverse image of the recessed portion 48 of band 14. Restated, shoulder element 52 of band 12 is at the right end of its recessed portion while shoulder element 52 of band 14 is at the left end of its respective recessed portion, whereby the neck elements 54 of the respective recessed portions, contrary to the convergence of FIG. 4A, extend generally parallel to each other as illustrated with dashed lines in FIG. 4B.

Figure 4C:
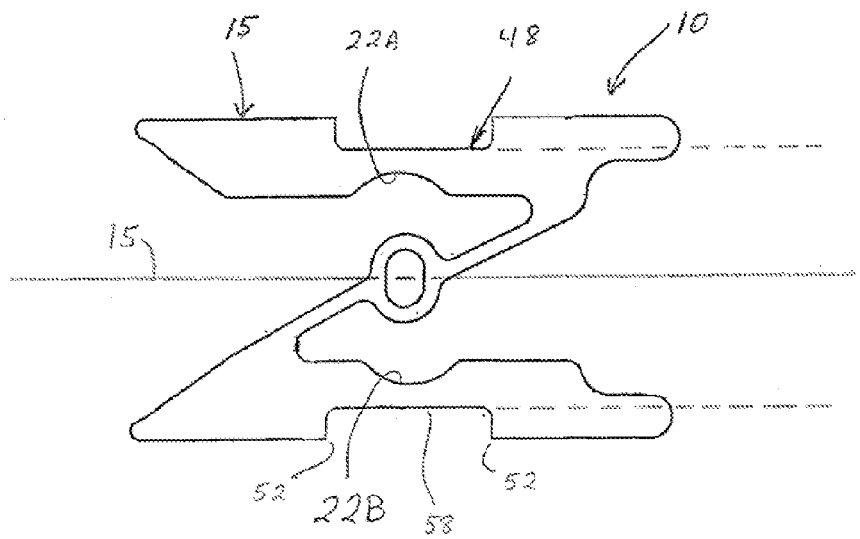
FIG. 4C shows a top view of a fifth embodiment of springs of the invention.
Figure 5:
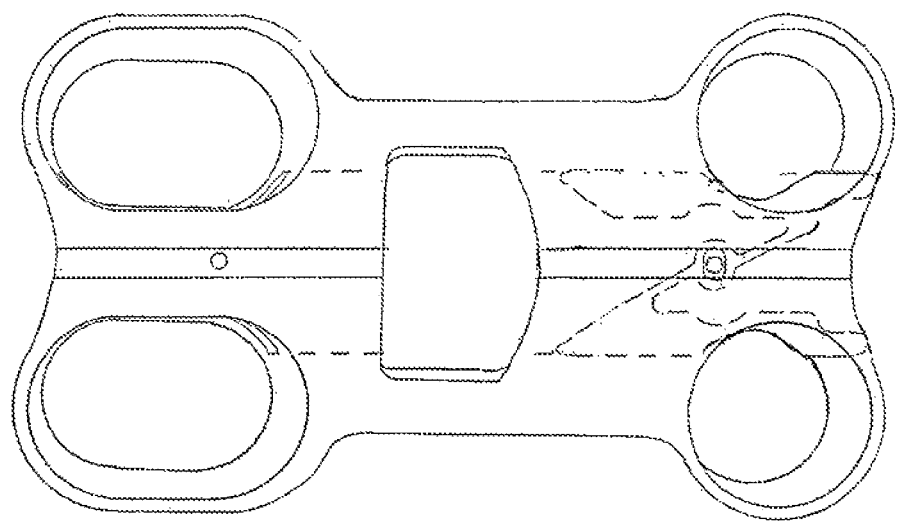
FIG. 5 shows a top view of a surgical plate as in FIG. 2, having a spring of FIG. 4A assembled thereto.

FIG. 4C shows a spring similar to the springs of FIGS. 4A and 4B, but wherein the recessed portions 48 are centered between the left and right ends of bands 12 and 14. Further, the configurations of recessed portions 48 are such that a given such recessed portion is internally symmetric, left-to-right, within its own design. Each recessed portion has a left end and a right end. An image or the profile of the recessed portion at the right end, when reversed and laid over the profile at the left end of the recessed portion, matches the profile at the left end of the recessed portion. In a recessed portion 48 of FIG. 4C, the shoulder element 52 at one end of the recessed portion is a mirror image of the shoulder element 52 at the opposing end of the respective recessed portion.

FIGS. 4A and 4B show shoulder element 52 as having a substantial radius of curvature while FIG. 4C shows the shoulder element turning a relatively sharp, e.g. right angle, corner.

In FIGS. 4A and 4B, the more deeply recessed elements of recessed portions 48 are defined by neck and relief elements 54, 56, extensions of which intersect longitudinal axis 15 relatively close to one or both ends of spring 10. By contrast, the more deeply recessed elements in FIG. 4C are defined by straight line bottom walls 58, extensions of which do not intersect longitudinal axis 15 near either end of spring 10 as illustrated with dashed lines in FIG. 4C.

FIG. 4D shows a spring having certain characteristics of the springs of FIGS. 4A-4C but wherein enlargement 20 of the spring leaf has been eliminated, and aperture 18 has been relocated to band 14. In the embodiment of FIG. 4D, the configuration of band 12 is the same as the configuration of band 12 in FIG. 4B. Relative to FIGS. 4A-4C, aperture 18 has been relocated to band 14. Accordingly, the top view of spring leaf 16 shows the leaf as extending in a straight line at a constant width from band 12 to band 14. Aperture 18 has been re-configured into a circular shape, and is shown generally centered between the innermost and outermost edges of band 14. Aperture 18 has further been reduced in size such that the cross-section/diameter of aperture 18 is only slightly larger than the cross-section/diameter of stud 44. Further, the width "W" of band 14 between aperture 18 and the remote end of the band is shown to be optionally less than the corresponding portion of the length of the left portion of band 12.

Springs 10 illustrated in FIGS. 1, 2, and 2A find use primarily when the axis of the bone screw, as driven, is substantially perpendicular to the upper surface of the spring. Bone screws can be effectively driven, and back-out, withdrawal of the bone screws, can be controlled by the spring bands at either or both of bands 12, 14.

Figure 6:
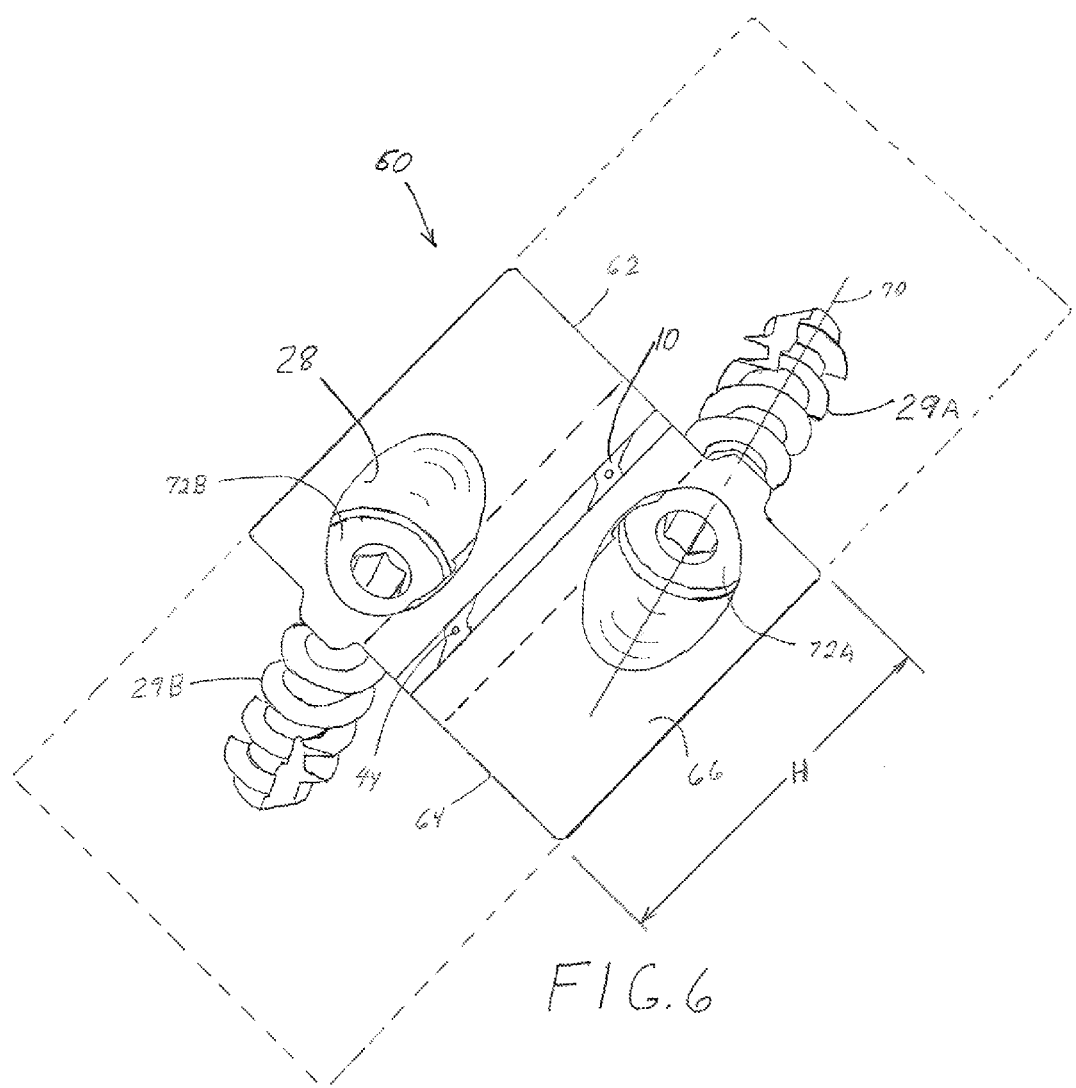
FIG. 6 shows a top view of a first relatively taller spinal cage assembly, including screws, and springs as in FIG. 4A.
Figure 7:
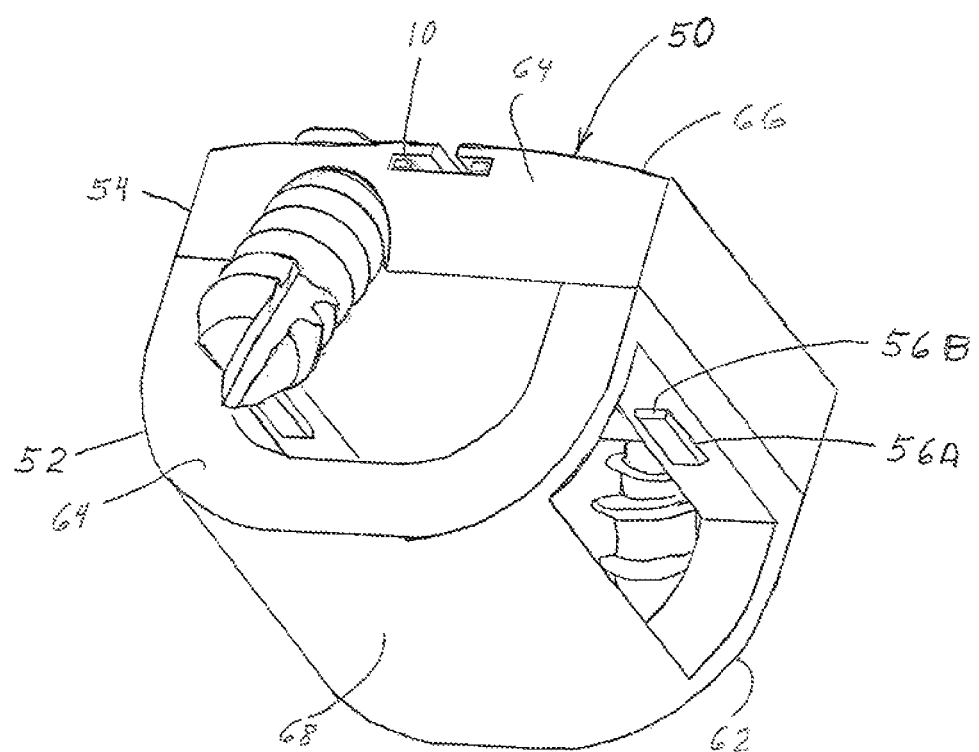
FIG. 7 shows a bottom pictorial view of the spinal cage assembly shown in FIG. 6.
Figure 8:
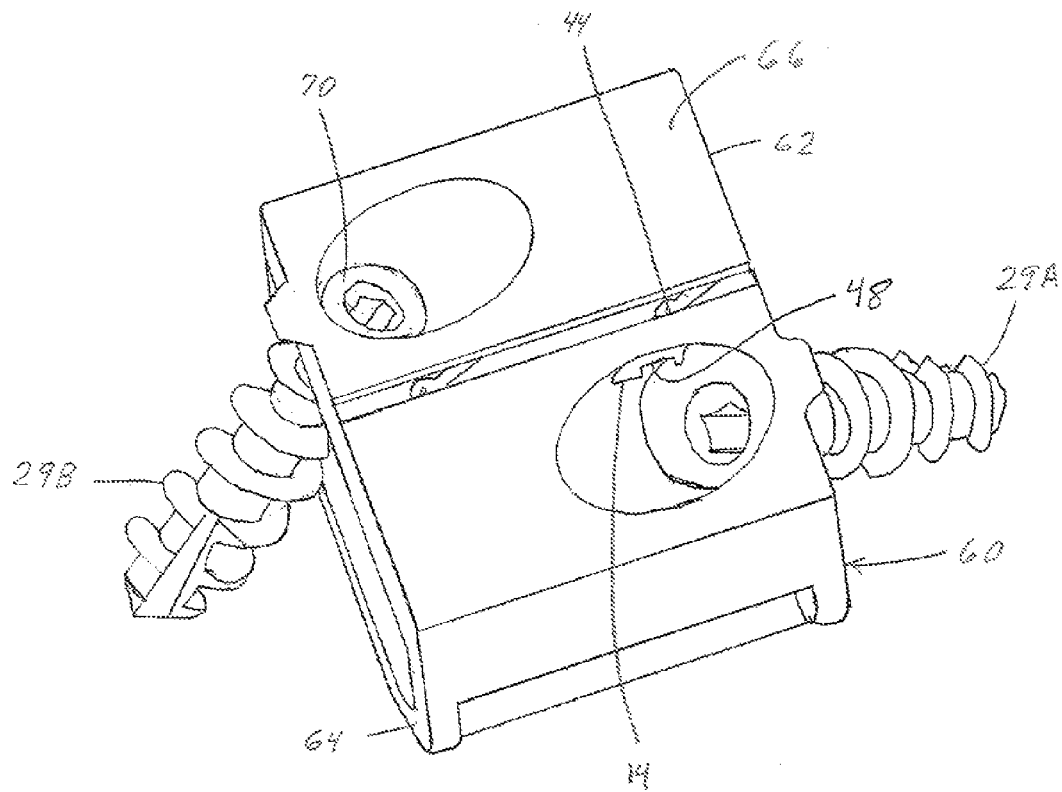
FIG. 8 shows a top pictorial view of the spinal cage assembly shown in FIGS. 6 and 7, but using a spring as shown in FIG. 4C.

Springs 10 illustrated in FIGS. 4A, 4B, 4C, and 4D are designed for use with spinal cages, where a bone screw is driven into overlying and underlying natural bone, where the axis of the bone screw passes through either the top or the bottom of the spinal cage as illustrated in e.g. FIGS. 6-8.

As seen in FIGS. 6-8, at least a vector of the length "LS" of the spring extends along the height "H" of the cage. Also as seen in FIGS. 6-8, at least a vector of the axis of the bone screw extends generally in the direction of the length of the spring and along the height "H" of the cage.

In the embodiments of FIGS. 4A and 4B, and as illustrated in FIG. 6, the spring is installed in the cage such that the axis 70 of the bone screw is generally parallel to neck element 54 of the recessed portion, whereby shoulder element 52 interferes with passage of the screw head. Thus, the screw shank passes through, and may be guided by, recessed portion 48, but without the advance of the screw being impeded by edges of the recessed portion as the bone screw is driven through a screw aperture 28.

However, shoulder element 52 is in the path of travel of the screw head such that, as the screw head is advanced past the shoulder element, the bottom surface of the screw head interacts with shoulder element 52, and thus pushes the shoulder element laterally sideways, which moves the respective band 12 or 14 sideways, which sideways movement compresses the respective band 12 or 14 toward the other band, moves the respective screw-head-impacted band closer to the other band. The overall result is that the spring experiences a compressive force as the screw head is driven past shoulder element 52. Meantime, neither the neck element nor the relief element need interact with the screw head though, in some embodiments, either or both of the neck element and the relief element can interact with the screw head.

Once the screw head moves past the spring, resilient forces in the spring material restore the spring band to its less-compressed, previous position, wherein at least the shoulder element is again in a position to interfere with the path of the screw head. Accordingly, the shoulder element 52, in its restored, less-compressed position, is effective to prevent the screw head from backing out of the natural bone into which it has been driven. Given the functions of the neck element and the relief element of allowing the screw shaft and the head to pass generally unimpeded, given the function of shoulder 52 to permit the screw head to be driven, but not withdrawn, the spring of FIG. 4A can be used with one or two bone screws, one at each of bands 12, 14, where both screws are angled either up or down from the cage implant. Whereas the shoulder elements 52 are disposed toward the same end of the spring in FIG. 4A, in FIG. 4B, the shoulder elements 52 are disposed toward opposite ends of the spring such that springs of FIG. 4B are typically designed for use with a cage where a single spring interfaces with two bone screws, one of which is directed upwardly and one of which is directed downwardly. In springs as in FIG. 4C, the symmetry of a recess 48 enables the spring to interface with bone screws at both of bands 12, 14, and each band accommodates the respective bone screw extending either upwardly into overlying natural bone or downwardly into underlying natural bone.

Thus, of the springs shown in FIGS. 4A, 4B, and 4C, springs as in FIG. 4C are more versatile in their variety of potential usages while springs of FIGS. 4A and 4B provide more specific guidance/direction to the screw shank and head.

FIGS. 6-13 illustrate uses of springs 10 in bone-replacement cages 60. FIGS. 6-8 illustrate such cage wherein the cage is to be implanted in a patient such that a top 62 of the cage is facing toward the patient's head and a bottom 64 of the cage is facing away from the patient's head. In such instance, a front surface 66 of the cage faces toward the front of the patient's body, while a rear surface 68 of the cage faces toward the rear of the patient's body.

A spinal cage is used to replace defective natural bone material in the spine of the patient, where the defective natural bone material has been removed, and the cage is inserted into the spine in place of the removed natural bone material. Thus, the cage takes the same body forces of weight, bending, and the like as were taken by the defective bone material that was removed.

The cage illustrated in FIGS. 6-8 includes a spring 10 as illustrated in FIG. 4C. The cage 60 assembly is implanted in the patient's spine between a naturally-occurring underlying vertebral bone and a naturally-occurring overlying vertebral bone.

In order to stabilize the cage in the spinal column, the cage must be affixed to remaining healthy bone material in the spinal column. Such healthy bone material is disposed both above and below the cage, but not in front of the cage. Thus, attachment of the cage to the spine amounts to directing bone screws upwardly and downwardly from the cage, as illustrated in FIGS. 6-8.

A first bone screw 29A is driven into the overlying vertebral bone, shown in dashed outline in FIG. 6. A second bone screw 29B is driven into the underlying vertebral bone as shown in dashed outline in FIG. 6. As illustrated in FIG. 6, when a first bone screw 29A is driven into the overlying natural bone, and the screw head is seated against the inner wall of aperture 18, the longitudinal axis 70 of bone screw 29A extends through the front and top surfaces of the cage. When the bone screw has been so driven, the screw head 72A has been driven past the respective spring band 14 such that the screw head compressed the spring as the head passed the spring and, after the screw head passed the band, the band resiliently returned to its more-relaxed position, thereby taking up a position blocking the return path of the screw head. Similarly, after the second bone screw 29B has been driven, the longitudinal axis of the second bone screw extends through the front and bottom surfaces of the cage. When the bone screw has been so driven, the screw head 72B has been driven past the respective spring band 12 such that the screw head compressed the spring as the head passed the spring and, after the screw head passed the band, the band resiliently returned to its more-relaxed position, thereby taking up a position blocking the return path of the screw head.

The angles of the bone screws 29A, 29B impose lateral forces on bands 12, 14 different from the lateral forces which accompany driving of the bone screws in implanting e.g. a cervical plate such as that illustrated in FIGS. 1-5. Straight outer edges of bands 12, 14 such as those shown in FIGS. 1-5 can interfere with the driving of the bone screws at such up and down angles to the front surface of the cage. However, recessed portions 48 in the outer edges of the bands, as illustrated in FIGS. 4A, 4B, 4C, 4D, 6, and 8 facilitate the driving of the bone screws in such upwardly and downwardly directions.

In the embodiments of FIGS. 6-8, a separate spring, anchored by a stud 44, is used for each bone screw aperture.

Figure 9:
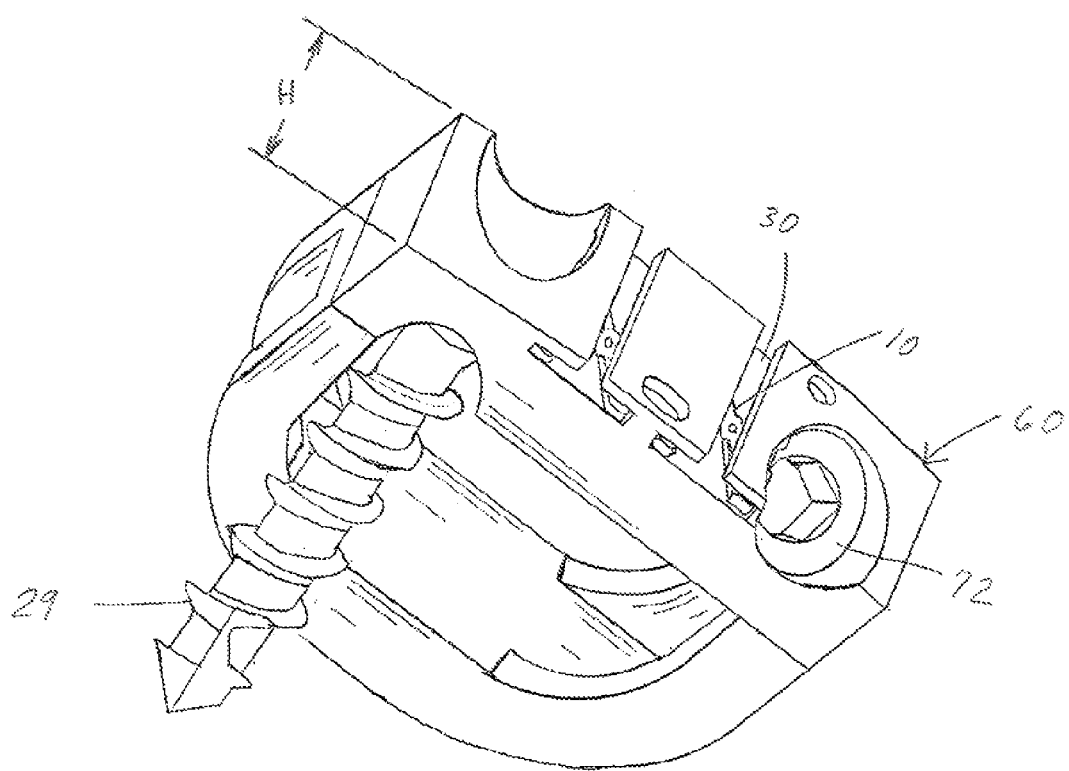
FIG. 9 shows a top pictorial view of a second relatively shorter spinal cage assembly, including two bone screws, and springs as in FIG. 4C.
Figure 10:
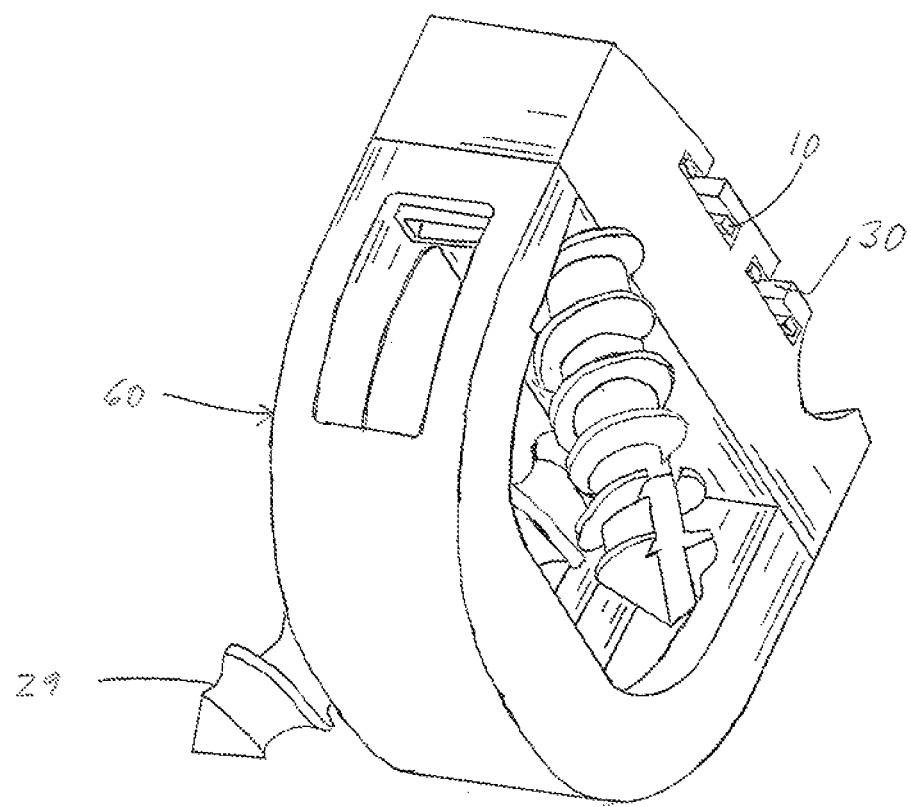
FIG. 10 shows a bottom pictorial view of the spinal cage assembly shown in FIG. 9.

FIGS. 9 and 10 show a cage as in FIGS. 6-8. However, the cage of FIGS. 9 and 10 is of relatively lesser height "H", and the springs 10 are side-by-side in first and second different channels 30, whereas the springs in FIGS. 6-8 are in a common channel which extends the full height of the cage. Accordingly, each spring 10 cooperates with, interacts with, only one bone screw.

The relatively shorter spinal cage implant 60 of FIGS. 9 and 10 is also representing an assembly of a cage body and an overlying plate. In this relatively shorter version of the spinal cage implant, the bone screw apertures 28 are necessarily side-by-side because of the limited height of the cage. In this instance, separate channels 30 are positioned side by side on the top, of the plate, receiving separate springs 10. Again, the bone screws are angled, one being angled up and one being angled down, relative to the top and bottom of the cage as implanted into the patient. Accordingly, the outer edges of the bands on the spring are recessed as illustrated in FIG. 4.

Figure 13:
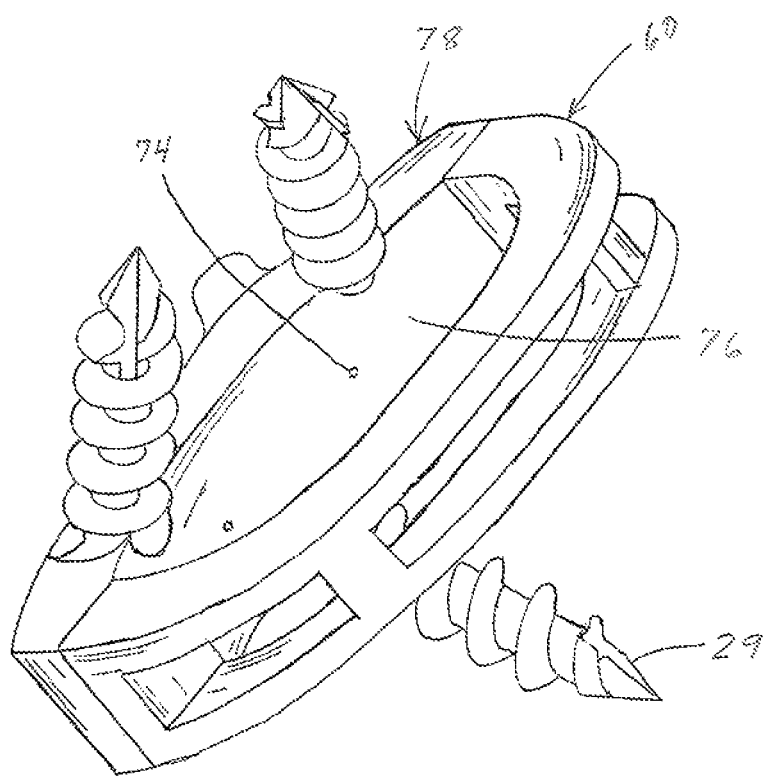
FIG. 13 shows a bottom pictorial view of the spinal cage assembly of FIG. 11, where the studs and/or stud welds are visible.

FIGS. 11, 12, and 13 show a third embodiment of spinal cage implant, also as a 2-part cage assembly having a cage body and a plate snap-assembled to the cage body.

The cage assembly of FIGS. 11, 12, and 13 is of relatively lesser height "H" as in FIGS. 9 and 10. However, in contrast to the cage of FIGS. 9 and 10 which show two bone screws and first and second open-top channels 30, the cage of FIGS. 11-13 has three bone screw apertures 28 and first and second closed-top channels 30A and 30B. Namely, other than observation ports 73, there is no channel opening along the front surface 66 of the cage. A first spring 10A corresponding to the spring of FIG. 4B is disposed in channel 30A.

The implant shown in FIGS. 11, 12, and 13 contemplates the use of three bone screws in the three apertures 28, two pointing a first direction up or down, and the third pointing in the opposing up or down direction.

Spring 10A is retained, laterally, in channel 30A by the confining top, bottom and side walls of the channel. Spring 10A is retained longitudinally in channel 30A by a stud 44A which extends through a stud aperture 42 in the top wall of the cage, from the bottom of the top wall of the cage upwardly through the bottom wall 32 of channel 30A. Stud 44A extends upwardly from the bottom wall of channel 30A and into leaf aperture 18 in spring leaf 16. Stud 44A is held in place in aperture 42 by a combination of (i) a friction fit between the stud and the stud aperture, and (ii) a spot weld 74 at the bottom surface 76 of the front wall 78 of the cage.

First and second bands 12, 14 of spring 10A extend into adjacent bone screw apertures 28A, 28B and interact with the corresponding first and second bone screws 29A, 29B as the screws are driven through the respective apertures 28A, 28B and into respective natural bone tissue of the patient.

Thus, as screw 29A is driven through aperture 28A, the shank of the screw is aligned with the aperture 28A such that the shank either does not contact the respective band 12A or the only contact is a guiding/glancing contact which imparts no material impedance to the advance of the screw. As the screw head 72A reaches band 12A, continuing advance of the screw head pushes band 12A laterally side/sideways so as to enable the head to move past the band.

As the band is pushed sideways, the band movement applies a lateral stress on the respective spring leaf 16. Turning to FIG. 4B, the lateral stress on spring leaf 16 is translated along the length of the spring leaf. The elongate shape of leaf aperture 18 enables the spring leaf to move relative to stud 44, in the direction of the width "WS" of the spring, such that the stresses in spring leaf 16 can be distributed along the full length of the spring leaf. If, by contrast, the spring leaf aperture 18 were confining/circular such that the leaf could not move relative to the stud, the stresses in the spring leaf would be confined to that (approximately half) portion of the spring leaf which would be between the stressed band and the spring leaf aperture. Thus, by providing aperture 18 as an elongate opening, with its longitudinal axis extending along the width "WS" of the spring, the stresses imposed on the band, as a bone screw head is driven past the band, are distributed along the full length of the spring leaf as well as being passed on to the opposing spring band, whereby the stresses imposed on one band are distributed along the full length of the spring leaf, as well as being distributed to the opposing band.

Returning to FIGS. 11, 12, and 13, a second spring 10B, corresponding to the spring illustrated in FIG. 4D, is disposed in the second channel 30B. As shown in FIG. 4D, spring 10B has a first working band 12 which interacts with the head of a bone screw illustrated as screw 29C in FIG. 12, and an anchoring band 14 which cooperates with a stud 44 in anchoring the spring to the cage. Bands 12 and 14 are connected to each other by spring leaf 16. Compared to the width "WB1" of band 12, anchoring band 14 has a relatively lesser-width "WB2". An enlarged portion of band 14 has a width corresponding generally to width "WB1" in accommodating aperture 18 through band 14. Aperture 18 in the embodiment of FIG. 4D is circular, and approximates the cross-section of the respective stud 44 which is to be used with spring 10C. Thus, the driving of a stud through stud aperture 42 of the front wall of the cage, and through aperture 18 in band 14, confines the spring laterally and longitudinally in the respective channel 30B. Namely, because aperture 18 has been positioned in band 14, there is no need for the spring to move relative to the stud in order for the stress imposed on band 12 to be distributed along the full length of the spring leaf, to band 14, whereby the full length and width of the spring can participate in absorbing the stress without need for movement of the spring relative to stud 44.

As illustrated in FIG. 12, adjacent screws 29A and 29B interact with the opposing bands 12, 14 of a first spring 10A; while screw 29C interacts with a band of a second spring 10B. FIG. 12 also illustrates that, where only one of the bands is used to interact with a bone screw, the band aperture 18 which interacts with stud 44 can be located in the non-screw-interacting band whereby the spring leaf need not have an enlargement 20 or the aperture 18. Rather the enlargement, if needed, is in the band which does not interact with the screw.

FIG. 13 shows welds 74 securing the studs to the plate at the bottom of the plate.

FIGS. 11-13 have been discussed in terms of the stud being spot-welded to the front wall of the cage. In any of the embodiments, the stud can be so-welded to the implant at the front wall of the cage, or at the bottom wall of an e.g. cervical plate. In such instance, the friction-fit of the stud in the stud aperture is of less importance because, given a reasonably close fit of the stud in the stud aperture, e.g. equivalent to no more than about 0.005 inch difference between stud diameter and aperture diameter, the spot weld can, alone, by itself, without other contribution, retain the stud in the necessary location, relative to the spring, in the respective implant.

By contrast, in some instances, the stud is held in the stud aperture entirely on the strength of the friction-fit of the stud in the stud aperture. In such instance, the stud is sized in cross-section such that the friction created when the stud is pressed into/through the stud aperture, is sufficient to hold the stud in the stud aperture with enough resistance to movement that the stud will not move relative to the stud aperture during the use life of the implant assembly.

In the alternative, any of the springs of the invention can be modified by removing leaf aperture 18 from either the spring leaf or band 14, with the addition of a protuberance extending laterally along the width of the spring from one or both of bands 12, 14. When the spring is being inserted longitudinally into the respective channel 30, the spring is squeezed to reduce the width of the spring enough that the protuberance or protuberances can enter the channel. As the spring is advanced along the length of the channel, the protuberances encounter corresponding and cooperating recesses, of similar configuration, and of limited length, in the side walls of the channel, and the restorative forces in the squeezed spring cause the spring to expand such that the protuberances move laterally into the recesses. Leading and trailing edges of the protuberances generally encounter corresponding leading and trailing edges of the recesses as the protuberances enter the recesses. With the spring thus expanded such that the protuberances extend into the recesses, the longitudinal positioning of the spring in the channel is fixed.

Respective such protuberances and recesses are taught in U.S. Pat. No. 7,008,426 Kamaljit S. Paul, herein incorporated by reference as to the teaching of such protuberances and recesses in a channel and spring.

Preferred method of fabricating the spring is to use laser cutting apparatus to cut away waste material so as to leave bands 12, 14 and spring leaf 16.

Since the surgical implants of the invention are to be implanted in living bodies, all materials used in the bone treatment plate assemblies must be compatible with, and safe for use inside, the living body. In that regard, known materials for bone treatment plate 24, spring structure 10, and stud 44, include, without limitation, stainless steel, titanium, or titanium alloy, for example titanium-aluminum alloy, or a nickel-titanium alloy commonly known as Nitinol. A specific titanium aluminum alloy referred to in ASTM F-136 is (Ti 6AL-4V). Other titanium alloys, compatible for use in the living body, are contemplated. In addition, certain polymeric materials are also known to be compatible for use in the living body, such as for example and without limitation, polyetheretherketone (PEEK). All such materials known to be compatible for use in the living body, and which embody the structural strength needed to sustain the stresses typically exerted in sue of such implants, are contemplated to be within the scope of the invention. Preferred materials for bands 12, 14 have a desired level of resilient flexural capacity. Safety is typically controlled by composition and structure.

The springs must perform the required physical functions of flexing enough, when properly positioned over apertures 28, to let the bone screws pass below the bands without exceeding the flexural limits, collectively, of the bands or the spring leaf, and must return to blocking positions over the screw heads after passage of the bone screws. Such flexural properties are based on physical properties inherent in the material compositions, in combination with the physical cross-sections of the bands and springs.

The resilient properties can be provided by bands 12, 14, by spring leaf 16, or by a combination of the bands and the spring leaf. Thus, bands 12, 14 can be substantially non-flexible and substantially all the resilience can be provided by the flexibility of spring leaf 16. In the alternative, spring leaf 16 can be substantially non-flexible, namely can perform a rigid blocking function once installed in channel 30, whereby most, or substantially all, of the resilience is provided by bands 12, 14. Typically, the ability of bands 12, 14 to move, in response to advance of a bone screw, is provided in part by each the band and the spring leaf.

In the embodiments where aperture 18 is elongate/slotted in the transverse/width direction, the spring leaf can move relative to stud 44 as part of the accommodation and movement of the spring in accommodating passage of the head of the bone screw.

The invention contemplates that bands 12, 14 can be arranged in other than a resting and straight condition when not being forced sideways by heads of bone screws. Thus, the bands can be under a degree of constant stress, e.g. pre-stressed condition, wherein the level of stress increases as the head of the screw passes, and then reverts to the previous, reduced, level of stress, or reverts to some other related stress, after the screw head passes. In general, spring 16, even without stress from a bone screw, typically exerts a relatively modest degree of force urging bands 12, 14 against the side walls 34 of channel 30.

The spring structure, including spring leaf 16 and bands 12, 14, is preferably fabricated from a single unitary, generally planar work piece, of generally uniform thickness "TS". In such instance, the thickness of the spring structure also is the height of the respective spring leaf 16.

In preferred expressions of this invention, but not as a limiting factor, the width "WSL" of spring leaf 16, as illustrated in FIGS. 4C and 4D, are less, preferably substantially less, than the thickness "TS" of the spring leaf. Restated, the average width "WSL" is less than the average thickness "TS". In preferred embodiments, the width "WSL" of the spring leaf is less than the thickness "TS" of the spring leaf. Thus, the ratio of width "WSL" to thickness "TS" is preferably less than 1/1. In typical embodiments, the WSL/TS ratio, for a given spring leaf is about 0.15/1 to about 0.7/1, whereas more preferred embodiments employ WSL/TS ratios of about 0.2/1 to about 0.5/1. Most preferred embodiments employ WSL/TS ratios of about 0.25/1 to about 0.35/1. Accordingly, the bending resistance of a given spring leaf in the width direction "WSL", e.g. in the rest plane of the spring structure, e.g. as the bands are squeezed toward each other, is less than the bending resistance of that spring in the thickness direction "TS", namely a direction which would take the springs out of the plane or planes of bands 12, 14.

As used herein, "plane" as applied to the spring structure, especially to bands 12, 14, includes moderately curved surfaces such as those illustrated in FIG. 3. However, the materials of both bands 12, 14 and spring leaf 16 are resilient whereby a truly flat planar structure can readily conform to the modest curvature of an implant 24 or 60 configured with modest curvature at the front surface of the plate of e.g. FIG. 3 or 7.

Given the rest magnitude of angle α, at least a substantial vector of the width "WSL" of the spring leaf is aligned with the width "WS" of the spring. Accordingly, given the relative bending resistances in the "WSL" and "TS" directions, when a force is exerted against the spring structure, generally along the direction of width "WS", thus to urge bands 12, 14 toward each other, the spring structure tends to respond by collapsing inwardly thereby to reduce width "WS" of the spring, and preferentially reducing the magnitude of angle α rather than distorting the spring out of its generally planar configuration. While suitably sensitive instrumentation can likely measure some three-dimensional distortion of the spring, such three-dimensional distortion preferably approximates zero. Meantime, change in angle α is desired to be substantial. Thus, the ratio of change in angle α relative to three-dimensional distortion of the spring, when a squeezing force, which is not a collapsing force, is exerted on band 12 and/or 14, is preferably substantially greater than 1/1 and can approach infinity. As the ratio of width "WSL" of the spring leaf to thickness of the spring leaf is increased, the ratio of such change in the respective angles decreases. Such ratio is preferably at least 3/1, more preferably at least 10/1.

By contrast, since resistance to bending in the "IS" direction is relatively greater than resistance to bending in the "WSL" direction, namely bending the spring leaf in the relatively larger "TS" dimension of the spring is more difficult than bending the spring in the relatively smaller "WSL" dimension of the spring, the bands tend to remain in a generally common plane while the bands move into a converging/diverging relationship with respect to each other when a compressive/squeezing force is applied to the outer edges of the spring structure.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. For use in a bone repair implant, a spring structure having a first spring structure end and a second spring structure end, a spring structure length (LS) and a spring structure width (WS), an imaginary transverse centerline extending across the width of said spring structure and thereby defining a first half of said spring structure corresponding to the first spring structure end, and a second half of said spring structure corresponding to the second spring structure end, said spring structure further having a spring structure top and a spring structure bottom, said spring structure comprising:
   (a) a first band having a first band length extending along the spring structure length, and a first band width extending along the spring structure width, a first band end disposed in the first half of said spring structure and a second band end disposed in the second half of said spring structure;
   (b) a second band having a second band length extending along the spring structure length, and a second band width extending along the spring structure width, a third band end disposed in the first half of said spring structure and a fourth band end disposed in the second half of said spring structure; and
   (c) a spring leaf extending from said first band in the first half of said spring structure to said second band in the second half of said spring structure.

2. A spring structure as in claim 1 wherein an aperture extends through said spring leaf.

3. A spring structure as in claim 2 wherein said spring leaf extends in a generally constant direction from said first band to said second band.

4. A spring structure as in claim 2, spring structure material entirely surrounding the aperture such that lateral entry into the aperture is precluded by the surrounding spring structure material, and wherein said spring leaf extends in a first direction from said first band to the aperture, and in a second substantially different direction from the aperture to said second band.

5. A spring structure as in claim 3, spring structure material entirely surrounding the aperture such that lateral entry into the aperture is precluded by the surrounding spring structure material, and wherein the aperture has a length and a width, the length of the aperture being greater than the width of the aperture.

6. A spring structure as in claim 4 wherein the aperture has a length and a width, the length of the aperture being greater than the width of the aperture.

7. A spring structure as in claim 2, spring structure material entirely surrounding the aperture such that lateral entry into the aperture is precluded by the surrounding spring structure material, and said spring leaf having a spring leaf width (WSL), further comprising a substantial enlargement of the spring leaf width at the aperture.

8. A spring structure as in claim 2 wherein the aperture has a length and a width, the length of the aperture being greater than the width of the aperture.

9. A spring structure as in claim 8, said first band having an inner edge facing inwardly into said spring structure and toward the aperture, further comprising a recess in the inner edge of said first band proximate, and facing, the aperture, thereby to accommodate movement of said spring leaf, at the aperture, into such recess.

10. A spring structure as in claim 1, further comprising an aperture extending through said spring structure, from the top of said spring structure to the bottom of said spring structure.

11. A spring structure as in claim 10, spring structure material entirely surrounding the aperture such that lateral entry into the aperture is precluded by the surrounding spring structure material, and wherein the aperture extends through one of said first and second bands.

12. A spring structure as in claim 11, said one of said first and second bands having a band width (WB2), further comprising a substantial enlargement of the band width at the aperture.

13. A spring structure as in claim 1, the outer edge of said first band having a first outermost edge portion which, in part, defines the width of said spring structure, and a first recessed portion, said first recessed portion being located intermediate the length of said spring structure and spaced from both of the first and second ends of said spring structure.

14. A spring structure as in claim 13, said first recessed portion being internally symmetric such that a profile of a longitudinally extending first half of said first recessed portion can be overlaid over a profile of a longitudinally extending second half of said first recessed portion, and the profile of the overlying first half of said first recessed portion substantially matches the profile of the underlying second half.

15. A spring structure as in claim 13, said first recessed portion of said first band comprising a first shoulder element extending, in a first direction, from a first end thereof at the outermost edge of said first band to a second end thereof, a first intermediate neck element having a third end extending, in a second direction, from the second end of said shoulder element, away from said first outermost edge, to a fourth end, and a first relief element having a fifth end extending, in a third direction, from said first neck element toward the outermost edge of said first band.

16. A spring structure as in claim 15, the outer edge of said second band having a second outermost edge portion which, in part, defines the width of said spring structure, the outer edge of said second band further having a second recessed portion, said second recessed portion of said second band comprising a second shoulder element extending, in a fourth direction, from a sixth end at the outermost edge of said second band to a seventh end, a second intermediate neck element having an eighth end extending, in a fifth direction, from the seventh end of said second shoulder element, away from said second outermost edge to a ninth end, and a second relief element having a tenth end extending from said second neck element, in a sixth direction, toward the outermost edge of said second band.

17. A spring structure as in claim 16 wherein said first and second shoulder elements are disposed toward the first end of said spring structure.

18. A spring structure as in claim 16 wherein said first and second shoulder elements are disposed toward opposing ones of the first and second ends of said spring structure.

19. A spring structure as in claim 1, spring structure material entirely surrounding the aperture such that lateral entry into the aperture is precluded by the surrounding spring structure material.

20. A bone repair implant assembly comprising an implant body having a length, and an implant wall defining a top of said implant body, a channel extending along the length of said implant body in said implant wall, said channel having a bottom wall, opposing side walls, and a top wall, a stud aperture extending into said implant wall from the bottom wall of said channel, a spring structure as in claim 1 being disposed in said channel, an aperture in said spring structure overlying the stud aperture.

21. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 2 being disposed in said channel with the aperture in said spring structure overlying the stud aperture, a stud being fixedly positioned in said stud aperture and extending into the aperture in said spring structure.

22. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 3 being disposed in said channel with the aperture in said spring structure overlying the stud aperture, a stud being fixedly positioned in said stud aperture and extending into the aperture in said spring structure.

23. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 4 being disposed in said channel with the aperture in said spring structure overlying the stud aperture, a stud being fixedly positioned in said stud aperture and extending into the aperture in said spring structure.

24. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 5 being disposed in said channel with the aperture in said spring structure overlying the stud aperture, a stud being fixedly positioned in said stud aperture and extending into the aperture in said spring structure.

25. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 6 being disposed in said channel, an aperture in said spring structure overlying the stud aperture, a stud being fixedly positioned in said stud aperture and extending into the aperture in said spring structure.

26. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 11 being disposed in said channel, an aperture in said spring structure overlying the stud aperture, a stud being fixedly positioned in said stud aperture and extending into the aperture in said spring structure.

27. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 13 being disposed in said channel, an aperture in said spring structure overlying the stud aperture, a stud being fixedly positioned in said stud aperture and extending into the aperture in said spring structure.

28. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 14 being disposed in said channel, an aperture in said spring structure overlying the stud aperture, a stud being fixedly positioned in said stud aperture and extending into the aperture in said spring structure.

29. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 15 being disposed in said channel, an aperture in said spring structure overlying the stud aperture, a stud being fixedly positioned in said stud aperture and extending into the aperture in said spring structure.

30. A bone repair implant assembly comprising an implant body having a length, and an implant wall defining a top of said implant body, a channel extending along the length of said implant body in said implant wall, said channel having a bottom wall and opposing side walls, a stud aperture extending into said implant wall from the bottom wall of said channel, a spring structure as in claim 18 being disposed in said channel, an aperture in said spring structure overlying the stud aperture, a stud being fixedly positioned in said stud aperture and extending into the aperture in said spring structure.

31. A bone repair implant assembly as in claim 20, further comprising a bone screw extending through a bone screw receiving aperture in said implant body arid interacting with said spring structure, further comprising a second said spring structure as in claim 1 disposed in said channel, an aperture in said second spring structure overlying a second stud aperture which extends into said implant wall of said implant body from the bottom wall of said channel, a second stud being fixedly positioned in said second stud aperture and extending into the aperture in said second spring structure, a second bone screw extending through a second bone screw receiving aperture in said implant body and interacting with said second spring structure.

32. A bone repair implant assembly as in claim 20, further comprising a bone screw extending through a bone screw receiving aperture in said implant body and interacting with said spring structure, further comprising a second channel extending along the length of said implant body in said implant wall, said second channel having a second bottom wall and second opposing side walls, a second stud aperture extending into said implant wall from the bottom wall of said second channel, a second spring structure as in claim 8 being disposed in said second channel, an aperture in said second spring structure overlying the second stud aperture, a second stud being fixedly positioned in said second stud aperture and extending into the aperture in said second spring structure, a second bone screw extending through a second bone screw receiving aperture in said implant body and interacting with said second spring structure.

33. For use in a bone repair implant, a spring structure having first and second spring structure ends, a length and a width, an imaginary transverse centerline extending across the width of said spring structure and thereby defining a first half of said spring structure corresponding to the first spring structure end, and a second half of said spring structure corresponding to the second spring structure end, said spring structure comprising:
(a) first and second bands, said bands having respective first and second band ends corresponding to the first and second spring structure ends,
(b) a spring leaf extending from said first band in the first half of said spring structure in a direction toward said second band in the second half of said spring structure to an aperture in said leaf, said leaf continuing from the aperture toward said second band in the first half of said spring structure, spring materials entirely surrounding the aperture in said leaf such that lateral entry into the aperture is precluded by the surrounding spring structure material.

34. A spring structure as in claim 33 wherein the aperture has a length and a width, the length of the aperture being greater than the width of the aperture.

35. A spring structure as in claim 33, said spring leaf having a spring leaf width (WSL), further comprising a substantial enlargement of the spring leaf width at the aperture.

36. A bone repair implant assembly comprising an implant body having a length, and an implant wall defining a top of said implant body, a channel extending along the length of said implant body in said implant wall, said channel having a bottom wall, opposing side walls, and a top wall, a stud aperture extending into said implant wall from the bottom wall of said channel, a spring structure as in claim 33 being disposed in said channel with the aperture in said spring structure overlying the stud aperture, a stud being fixedly positioned in said stud aperture and extending into the aperture in said spring structure.

37. A bone repair implant assembly comprising an implant body having a length, and an implant wall defining a top of said implant body, a channel extending along the length of said implant body in said implant wall, said channel having a bottom wall, opposing side walls, and a top wall, a stud aperture extending into said implant wall from the bottom wall of said channel, a spring structure as in claim 34 being disposed in said channel with the aperture in said spring structure overlying the stud aperture, a stud being fixedly positioned in said stud aperture and extending into the aperture in said spring structure.

38. A bone repair implant assembly comprising an implant body having a length, and an implant wall defining a top of said implant body, a channel extending along the length of said implant body in said implant wall, said channel having a bottom wall, opposing side walls, and a top wall, a stud aperture extending into said implant wall from the bottom wall of said channel, a spring structure as in claim 35 being disposed in said channel with the aperture in said spring structure overlying the stud aperture, a stud being fixedly positioned in said stud aperture and extending into the aperture in said spring structure.

39. A bone repair implant assembly comprising an implant body having a length, and an implant wall defining a top of said implant body,
   a channel extending along the length of said implant body in said implant wall, said channel having a bottom wall, opposing side walls, and a top wall, a stud aperture extending into said implant wall from the bottom wall of said channel,
   a spring structure being disposed in said channel, said spring structure having first and second ends, a length, and a width, a spring structure top and a spring structure bottom, said spring structure comprising
      first and second bands, each having a band top associated with the spring structure top, and a band bottom associated with the spring structure bottom, said bands having respective first and second ends corresponding to the first and second ends of said spring structure,
      a spring leaf extending between said first and second bands, said spring leaf having a leaf top and a leaf bottom, and an aperture extending through said spring structure, from the top of said spring structure to the bottom of said spring structure, spring material entirely surrounding the aperture.

40. A bone repair implant assembly as in claim 39, spring structure material surrounding the spring aperture such that lateral entry into the aperture is precluded by surrounding spring structure material.

41. A spring structure as in claim 5 wherein the length of the aperture extends along the width of said spring structure.

42. A spring structure as in claim 39, the aperture having a length and a width, the aperture length being greater than the aperture width, the aperture length extending along the width of said spring structure.

43. A spring structure as in claim 8 wherein the length of the aperture extends along the width of said spring structure.

44. A spring structure as in claim 33 wherein the length of the aperture extends along the width of said spring structure.

45. A bone repair implant assembly as in claim 20 wherein the aperture in said spring structure overlies the stud aperture, a stud being fixedly positioned in said stud aperture and extending into the aperture in said spring structure.

46. An implant assembly as in claim 39, a stud being fixedly positioned in said stud aperture and extending into, and fitting loosely, the aperture in said spring structure.

47. An implant assembly as in claim 21, said stud fitting loosely into the aperture in said spring structure.

48. An implant assembly as in claim 23, said stud fitting loosely into the aperture in said spring structure.

49. An implant assembly as in claim 25, said stud fitting loosely into the aperture in said spring structure.

50. An implant assembly as in claim 27, said stud fitting loosely into the aperture in said spring structure.

51. An implant assembly as in claim 37, said stud fitting loosely into the aperture in said spring structure.

52. An implant assembly as in claim 21, said stud fitting loosely into the aperture in said spring structure.

53. For use in a bone repair implant, a spring structure having a first spring structure end and a second spring structure end, a spring structure length and a spring structure width, said spring structure further having a spring structure top and a spring structure bottom, said spring structure comprising:
   (a) a first band having a first band length extending along the spring structure length, and a first band width extending along the spring structure width, the first band length being greater than the first band width, a first band end portion disposed toward the first end of said spring structure, and a second band end portion disposed toward the second end of said spring structure;
   (b) a second band having a second band length extending along the spring structure length, and a second band width extending along the spring structure width, a third band end portion disposed toward the first end of said spring structure and a fourth band end portion disposed toward the second end of said spring structure; and
   (c) a spring leaf extending from said first band and away from the first spring structure end and extending toward, and connecting to, the second spring structure end portion.

* * * * *